(12) United States Patent
Nurmi et al.

(10) Patent No.: US 8,394,288 B2
(45) Date of Patent: Mar. 12, 2013

(54) USE OF SOLID BETAINE PRODUCT AND METHOD FOR ITS MANUFACTURE

(75) Inventors: Juha Nurmi, Kirkkonummi (FI); Kirsti Jutila, Espoo (FI); Hannu Paananen, Kantvik (FI); Kristian Eriksson, Masku (FI)

(73) Assignee: Dupont Nutrition Biosciences APS, Copenhagen K (DK)

( * ) Notice: Subject to any disclaimer, the term of this patent is extended or adjusted under 35 U.S.C. 154(b) by 0 days.

(21) Appl. No.: 13/319,179

(22) PCT Filed: May 6, 2010

(86) PCT No.: PCT/FI2010/050369
§ 371 (c)(1),
(2), (4) Date: Jan. 18, 2012

(87) PCT Pub. No.: WO2010/128212
PCT Pub. Date: Nov. 11, 2010

(65) Prior Publication Data
US 2012/0112120 A1    May 10, 2012

(30) Foreign Application Priority Data

May 8, 2009   (FI) .................................... 20095522

(51) Int. Cl.
| C09K 3/18 | (2006.01) |
| C07C 229/12 | (2006.01) |
| C07C 227/40 | (2006.01) |
| E01H 10/00 | (2006.01) |
| B01J 2/30 | (2006.01) |

(52) U.S. Cl. ............ 252/70; 106/13; 562/553; 562/554; 562/575

(58) Field of Classification Search .................... 252/70; 106/13; 562/553, 554, 575
See application file for complete search history.

(56) References Cited

U.S. PATENT DOCUMENTS

| 1,901,111 A | 3/1933 | Masuda et al. |
| 3,240,558 A | 3/1966 | Heiss et al. |
| 4,359,430 A | 11/1982 | Heikkila et al. |
| 5,127,957 A | 7/1992 | Heikkila et al. |
| 5,795,398 A | 8/1998 | Hyoky et al. |
| 6,080,330 A | 6/2000 | Bloomer |
| 6,187,204 B1 | 2/2001 | Heikkild et al. |
| 6,572,775 B2 | 6/2003 | Heikkila et al. |

FOREIGN PATENT DOCUMENTS

| EP | 0054544 B1 | 6/1982 |
| EP | 1015106 B1 | 7/2000 |
| FR | 2151076 A1 | 4/1973 |
| WO | WO2004/009727 A1 | 1/2004 |
| WO | WO2007/128878 A1 | 11/2007 |

OTHER PUBLICATIONS

Finnish Search Report dated Feb. 4, 2010 issued in FI20095522.

*Primary Examiner* — Anthony J Green
(74) *Attorney, Agent, or Firm* — Scully, Scott, Murphy & Presser, P.C.

(57) ABSTRACT

The invention relates to the use of solid betaine for de-icing and/or preventing slipperiness. The solid betaine comprises at least one non-betaine compound affecting water and/or moisture movement in said solid betaine. The invention further relates to a process for the manufacture of solid betaine. A suspension comprising betaine crystals is prepared from a feed liquid and the betaine crystals are separated and washed. The amount of wash liquid is adjusted in order to leave 0.5 to 10 w-% of at least one non-betaine compound in said solid betaine.

41 Claims, No Drawings

USE OF SOLID BETAINE PRODUCT AND METHOD FOR ITS MANUFACTURE

FIELD OF THE INVENTION

The invention relates to the use of solid betaine for de-icing and/or preventing slipperiness wherein the solid betaine comprises at least one non-betaine compound affecting water and/or moisture movement in said solid betaine. The invention further relates to a process for the manufacture of solid betaine. A suspension comprising betaine crystals is prepared from a feed liquid and the betaine crystals are separated and washed. The amount of wash liquid is adjusted in order to leave 0.5 to 10 w-% of at least one non-betaine compound in said solid betaine.

BACKGROUND OF THE INVENTION

The purpose of the ice-melting and de-icing agents is to disrupt and weaken the adhesion of the ice to the surface of pavement, after which the surface can more easily be mechanically cleaned. In general, ice-melting agents are used for de-icing treatment, optionally together with added thickeners in order to increase viscosity, as well as water, surfactants and corrosion inhibitors.

The prevention of ice-formation and slipperiness is extremely important at airports in order to maintain safe conditions. Sodium chloride and other chlorides used on roads to prevent slipperiness, cannot be used at airports, since they corrode the metal parts of the planes. Thereto chlorides have a harmful effect on groundwater quality, soil, vegetation and soil microfauna. Also the use of urea, which traditionally has been used for de-icing at airports, has partly been given up due to its significant environmental load. At present acetates, liquid potassium acetate and solid sodium acetate as well as formiates, potassium formiate and sodium formiate are widely used at airports. Although these are effective in de-icing and are less detrimental to the environment, they are also heavily corrosive on metals, carbon brakes and electrical equipment of airplanes and airports. In fact ice-melting agents based on acetate and formiate have been found to cause heavy corrosion in airplane materials, including carbon brakes, metal surfaces and mating metal-metal surfaces. Further especially acetate and formiate dissolve the bitumen part of asphalt, thus causing pavement erosion and slipperiness.

Since solid and often granular ice-melting agents are easily carried away from the intended surface under the influence of air flows, liquid ice-melting agents have been found to be the most usable form of ice-melting agent. The effect of granular ice-melting agents has been found to be very local and the required amount has been found to be higher than for a liquid or wetted substance. Granular substances are however required for thicker ice in order to melt the ice down to the surface before snowploughing or brushing the surface, for example for the runway of an airport.

One more recent ice-melting agent used in liquid form is Cryotech NX360™ (Cryotech) which contains sodium acetate together with propanediol (Susterra®, Cryotech). Another ice-melting agent used in liquid form is the use of betaine as an aqueous solution for the prevention of freezing of aircrafts and runways disclosed in EP 1034231 B1. WO 2007/128878 A1 relates to the improved effect obtained by the combination of betaine and at least one other de-icing agent for de-icing treatment.

However, although betaine has been found to be a more environmental friendly alternative than urea and a non-corrosive alternative compared to the acetate and formiates used, the melting capacity of betaine as an aqueous solution has not been altogether satisfactory. Further the precipitation of betaine in concentrated aqueous solutions as well as its highly hygroscopic nature has also limited its use.

The original betaine, N,N,N-trimethylglycine, is often called glycine betaine to distinguish it from other betaines that are widely distributed in microorganisms, plants and animals. In the glycine betaine three methyl groups are bonded to the nitrogen atom of the glycine molecule.

Betaine can be obtained, for example from sugar beet by chromatographic methods. U.S. Pat. No. 5,127,957 as well as U.S. Pat. No. 4,359,430 disclose methods for the recovery of betaine from molasses and U.S. Pat. No. 5,795,398 discloses the recovery of betaine from a beet-derived sucrose containing material. U.S. Pat. No. 6,572,775 relates to a chromatographic system and U.S. Pat. No. 6,187,204 to a method for the fractionation of molasses for inter alia recovery of betaine. All methods aim for good yield as well as a high purity of the product.

Betaine has a bipolar structure and is a highly hygroscopic substance which easily turns viscous, lumpy and poorly flowable in humid conditions. In order to improve the treating properties of these hygroscopic materials in general two different approaches are used. The material may be coated with for example oil or fats which protect against humid conditions or the material may be mixed with fluidity improvers or anti-agglomeration agents which do not protect against humidity but which improve the fluidity of betaine in dry conditions. According to FR 2151076 A1 which relates to a method of improving the hygroscopicity and fluidity of different solid hygroscopic materials, such material may be treated with a powder of a calcium, magnesium, zinc or aluminium salt of a higher fatty acid.

Treating anhydrous betaine crystals is disclosed in EP 1015106 B1 which relates to arranging a hydrophobic and moisture-proof layer of calcium stearate or hydrophobic silica on the surface of the particles. The melted, hot soap is sprayed onto the surface of the betaine crystals or the soap flakes are mixed together with the betaine particles and then mixed and heated. According to EP 1015106 B1 anhydrous betaine crystals are used as an animal feed additive, in fertilizers, in cosmetic skin care products, in pharmaceutical products as well as in food.

The prior art processes for preventing ice-formation and slipperiness are not altogether satisfactory. There is a need for a non-corrosive and environmentally friendly alternative for de-icing and for preventing slipperiness. The present invention aims at satisfying that need.

It should be noted that all documents cited in this text ("herein cited documents") as well as each document or reference cited in each of the herein-cited documents, and all manufacturer's literature, specifications, instructions, product data sheets, material data sheets, and the like, as to the products and processes mentioned in this text, are hereby expressly incorporated herein by reference.

SUMMARY OF THE INVENTION

The invention relates to the use of solid betaine for de-icing and/or preventing slipperiness. The solid betaine comprises at least one non-betaine compound affecting water and/or moisture movement in and/or out from said solid betaine. Since the non-betaine part of the solid betaine product affects the water and/or moisture movement thus affecting the lumping of the solid betaine the solid betaine is used without problems with humidity and lumpiness.

The solid betaine may be used in combination with a solution, preferably an aqueous solution, more preferably an aqueous de-icing solution, most preferably an aqueous solution comprising betaine or it may be used in combination with another ice-melting agent for example acetates, formiates, urea, propanediol or mixtures thereof.

The invention further relates to a process for the manufacture of solid betaine. A suspension comprising betaine crystals is prepared from a feed liquid and the betaine crystals are separated and washed. The amount of wash liquid is adjusted in order to leave 0.5 to 10 w-% of non-betaine in said solid betaine.

One way to prepare a solid betaine which does not become lumpy and hard over time is to prepare it from a crystallization feed liquid comprising one or more non-betaine compounds which affect water and/or moisture movement to and/or from the betaine crystals. Another way is coating of betaine crystals or betaine particulates with non-betaine affecting the way water and/or moisture moves through the formed protecting layer.

DETAILED DESCRIPTION OF THE INVENTION

The invention relates to the use of solid betaine for de-icing and/or preventing slipperiness. The solid betaine comprises at least one non-betaine compound affecting water and/or moisture movement in said solid betaine. Typically the solid betaine is crystalline monohydrate or anhydrous betaine or a mix thereof and/or non- or soft-lumping.

According to one embodiment of the invention the solid betaine is used in a coated form, where the solid betaine is coated with one or more non-betaine compounds in order to obtain a protecting layer which affects the water and/or moisture movement to and/or from the solid betaine. Suitable coatings are polymers such as polyvinyl alcohol (PVA), carboxymethyl cellulose (CMC) or other water-soluble polymers. Also other coatings suitable to be spread in the nature and for preventing slipperiness can be used. Typically the solid betaine is used in the form of crystals or particulates such as grains, granules, flakes and/or the like.

However, in another embodiment of the invention the treating properties of betaine crystals used are improved by adjusting the amount of one or more non-betaine compounds present during preparation and/or crystallization. The amount of non-betaine present in the prepared solid betaine is adjusted by adjusting the washing conditions. The washing conditions may be adjusted by adjusting the amount of wash liquid, the washing time or amount of washings. The non-betaine compounds affect the movement of water and/or moisture in and/or out from the prepared solid betaine. Typically the one or more non-betaine compounds can be found naturally for example in vinasse and/or molasses. Thus, one preferred solid betaine is prepared by adjusting the amount of non-betaine compounds in the crystallization feed liquid, by adjusting the washing conditions and by leaving an effective amount of one or more non-betaine compounds in the solid betaine. In one embodiment of the invention the solid betaine is prepared from a feed liquid comprising at least one non-betaine compound affecting water and/or moisture movement in said solid betaine.

In the present specification and claims, the following terms have the meanings defined below.

The term "betaine" which is used throughout the specification and claims refers to solid trimethylglycine. Typically the solid betaine is anhydrous or monohydrate crystalline betaine or a mix thereof.

The term "solid betaine" used in the present specification and claims refers to the solid betaine product comprising betaine and non-betaine. The mean particle size is preferably from 0.3 to 4 mm. For the use for de-icing and/or preventing slipperiness the mean particle size of the solid betaine is preferably 0.5 to 4 mm, more preferably 0.8 to 2.5 mm and most preferably 1 to 1.5 mm. The mean particle size is preferably about 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or above, even up to about 3 or 4 mm. Since the particle size distribution typically follows a Gaussian distribution the solid betaine of a certain mean particle size comprises some amounts of crystals or particulates of smaller or bigger size.

The term "non-betaine" and "non-betaine compound" used in the present specification and claims refer to all other compounds than betaine present in the solid betaine used and prepared according to the invention. One, some or all of the non-betaine compounds affect the water and/or moisture movement to and/or from the solid betaine. The one or more non-betaine compounds may be impurities which are present or are found in molasses and/or vinasse and which therefore are readily present in a crystallization feed liquid used for the preparation and/or crystallization of betaine or they may be added during the preparation or processing, such as granulation of synthetic or natural betaine. The one or more non-betaine compounds may also be coated on the surface of solid betaine either on betaine crystals or on betaine particulates (including betaine granules, flakes etc).

The term "lumpy" or "lumpiness" refers to the property of betaine crystals to lump or clod in humid conditions. In the present invention lumping is tested by checking the lumping over time. In order to be possible to use in equipment normally used for spreading out solid de-icing agents in humid conditions the solid betaine needs to be possible to store over time without being stiffened, hard or lumpy.

The term "non or soft lumping betaine" refers to solid betaine in which only soft lumps which break easily are formed. The soft lumps can be crushed easily between the fingers or by hand pressure (pressure below 5 MPa, preferably below 3 MPa, most preferably below 2 MPa). The solid betaine is considered non- or soft lumping if the product has still not got lumpy after one month, i.e. possible lumps formed can be crushed by finger and/or hand pressure.

The term "humid conditions" refers to normal indoor and outdoor humidity (between 30 and 95%), i.e. the relative humidity defined as the ratio of the partial pressure of water vapor in a gaseous mixture of air and water vapor to the saturated vapor pressure of water at a given temperature. Humidity is a measure of the amount of water vapor in the air, not including any liquid water or ice falling through the air.

The "purity" of the product or feed liquid used or prepared for the preparation of solid betaine is counted compared to the dry substance by HPLC with resin in $Na^+$ or $Ca^{2+}$ form. The amount of water bound within and/or to the crystals is not taken into account. Due to differences in their crystal structure the anhydrous form bind more impurities to the crystal structure than the monohydrate crystal form.

In one embodiment of the invention the solid betaine used for de-icing and/or preventing slipperiness comprises 90 to 99.5 w-% of betaine and 0.5 to 10 w-% of non-betaine (of the dry substance not containing crystal water and/or free water). Typically the betaine is crystalline monohydrate or anhydrous betaine or a mix thereof. According to another embodiment the solid betaine comprises 0.1 to 7 w-%, preferably 0.1 to 5 w-%, more preferably 0.1 to 2 w-%, most preferably 0.1 to 1 w-% (of the dry substance) of one or more non-betaine compounds affecting water and/or moisture movement in said solid betaine. The non-betaine typically forms a covering film or layer around the betaine crystals, thus affecting the movement of moisture and/or water into and/or out from the solid betaine. Typically the one or more non-betaine compounds used are found in molasses or vinasse and are glycerol-like compounds, not as hygroscopic as betaine chosen from one or more of glycerol, erythritol, mannitol, sorbitol, inositol, fructose, glucose and propanediol. Typically the solid betaine is stored and/or used in humid conditions.

Suitable raw materials that may be present in the feed solution used for the preparation of betaine include molasses, vinasse, beet-derived juices, fermentation broths containing various organic acids, such as citric acid. Highly preferred raw materials include molasses and vinasse. The molasses are selected from the group consisting of beet molasses, stillage, vinasse, wheat molasses, barley molasses, corn molasses and solutions derived from any of the preceding.

Synthetic betaine may also be used in the present invention. According to one embodiment of the invention one or more non-betaine compounds for example similar to those present in molasses and/or vinasse are used and added to the preparation or crystallization feed liquid of the synthetic preparation process in order to prepare solid betaine comprising at least one non-betaine compound affecting the water and/or moisture movement to and/or from the solid betaine.

Typically the solid betaine for de-icing and/or preventing slipperiness of the present invention is used as such in solid form, but in a preferred embodiment the solid betaine is used in combination with a solution, preferably an aqueous solution, more preferably an aqueous de-icing solution comprising 35 to 65 w-%, most preferably 45 to 65 w-% of water. The ratio of solution compared to solid betaine used is typically between 0 and 80 w-%, preferably 0 to 70 w-%, most preferably 0 to 50 w-%.

According to one embodiment of the invention the solid betaine is used in combination with a solution comprising betaine.

In one embodiment the solid betaine is used at the same time as the solution. In another embodiment the solid betaine is used before the solution and in a third embodiment the solution is used before the solid betaine. Typically the solid betaine is used in combination with a solution comprising 45 to 55 w-%, preferably about 50 w-% of betaine. Typically the betaine of this solution is a solid betaine as described in the examples, a commercially available betaine product, such as BETAFIN® or Nutristim®, Finnfeeds Finland Ltd, liquid betaine solutions from chromatographic separations or for example synthetic betaine.

In a further embodiment of the invention the solid betaine is used in combination with another ice-melting agent selected from the group consisting of acetates, formiates, urea, propanediol and mixtures thereof. The other ice-melting product is typically used in solid form or in the form of a solution before, after or at the same time as the solid betaine.

For de-icing and/or preventing slipperiness the solid betaine product according to the invention is applied to the desired application target, including airports, roads, bridges, stairs, yards, pavements and ramps, as well as certain special road sections that require de-icing treatment. The betaine product of the invention is used in solid form as such or together with an aqueous solution in an amount that is sufficient to provide an efficient effect in regard to de-icing and preventing slipperiness. The betaine product of the invention is also used for diminishing the corrosive effect of other de-icing agents, for diminishing the negative effects of ice-melting agents on pavement durability on the treated target, for diminishing the detrimental effects of ice-melting agents on the environment, for decreasing the effect of ice-melting agents on the wear of the components of the carbon composite breaks used in airplanes, for decreasing the pollution of the groundwaters caused by ice-melting agents and for diminishing the migration of polyaromatic hydrocarbon (PAH) compounds into the environment caused by ice-melting agents.

Further the invention relates to a process for the manufacture of a solid betaine, typically crystalline monohydrate or anhydrous betaine or a mix thereof and/or non- or soft-lumping betaine, comprising 90 to 99.5 w-% of betaine of the dry substance. The process comprises preparing a suspension comprising betaine crystals from a feed liquid. The feed liquid is typically originating from molasses or vinasse. The crystals are then separated and washed with a wash liquid and the wash conditions are adjusted in order to leave non-betaine in the solid betaine product in an amount of 0.5 to 10 w-% of the dry substance. In a preferred embodiment the solid betaine comprises 0.1 to 7 w-%, preferably 0.1 to 5 w-%, more preferably 0.1 to 2 w-%, most preferably 0.1 to 1 w-% of the dry substance of one or more non-betaine compounds affecting the water and/or moisture movement in said solid betaine. Typically the non-betaine are impurities normally found in molasses or vinasse which both can be used as feed liquid for the recovery of betaine. Typically the non-betaine compounds are glycerol-like impurities not as hygroscopic as betaine chosen from one or more of glycerol, erythritol, mannitol, sorbitol, inositol, fructose, glucose or propanediol.

Typically the feed liquid comprises 5 to 45 w-% of non-betaine and the amount of wash liquid is proportional to the amount of impurities in the feed liquid.

In one embodiment of the invention the drying of the solid betaine is performed in a drum drier and in another embodiment the drying is performed in an oven and in a third embodiment by adding air to a screw conveyor used for transporting a product of said betaine crystals. The embodiments may be combined.

In a further embodiment of the invention the manufacture of the solid betaine further comprises granulating betaine and/or coating of the solid betaine. Typically the solid betaine, in the form of betaine crystals or particulates is coated with a polymer, preferably polyvinyl alcohol (PVA), carboxymethyl cellulose (CMC) or other water-soluble polymers.

The mean particle size of the solid betaine is typically 0.5 to 4 mm, more preferably 0.8 to 2.5 mm and most preferably 1 to 1.5 mm. The mean particle size is preferably about 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or above, even up to about 3 or 4 mm.

In a preferred embodiment of the invention a low purity feed crystallization (yield crystallization) is used for the preparation of solid betaine. Normally crystals formed during yield crystallization are dissolved and fed back to the feed liquid of the product crystallization and yield crystallization is only performed in order to diminish the amount of liquid which need to be extracted. One advantage of this embodiment is that the crystalline solid betaine prepared from the feed crystallization may be used as such and do not even need to be completely washed or dried before use. The amount of wash needed depends on the size of the crystals, on the purity of the feed liquid and on the equipment used. Typically larger crystals need less washing and drying. Solid monohydrate or anhydrous betaine may also be used as an animal feed additive, in fermentation processes, in cosmetics, in fertilizers or in food products.

The following examples are given to further illustrate the invention and are not intended to limit the scope thereof. Based on the above description a person skilled in the art will be able to modify the invention in many ways to prepare solid betaine for the use of de-icing and preventing slipperiness.

EXAMPLE 1

Betaine Product from Vinasse

The raw material of this test was vinasse from Cristal Union (CU). The CU-vinasse was separated in a SMB-pilot (simulated moving bed) by combination of SMB SAC (Na+) (softening cation) and WAC (H+) (weak acid cation). The color and turbidity properties as well as the betaine and the glycerol content of the feed liquid are shown in Table 1.

TABLE 1

Feed liquid properties, Example 1

| Color* ICUMSA | Turbidity ICUMSA | Betaine (HPLC: Na$^+$/Ca$^{2+}$) | Glycerol (HPLC: Na$^+$) |
|---|---|---|---|
| 10563 | 1630 | 81.9/81.0 | 10.1 |

*The color was measured by an ICUMSA method (pH 7 and 0.45 µm filtration) and the turbidity is the difference between a non filtrated and a filtrated sample.

The test was carried out in a small Büchi rotavapor including a heating bath, vacuum system and controller. A 3-liter evaporation flask was used in all tests. At first the feed liquid was heated to 95° C. The evaporation was started by increasing the temperature to 115° C. The pressure was slowly decreased until it reached about 250 mbar. Although there was some foam formation in the beginning an anti-foam agent was not needed. The goal dry substance of 85-88 w-% was estimated visually and by calculation of the amount of condensate. The total residence time for the crystallization was 24 hours. After the evaporation the temperature was set to 95° C. for centrifuging.

The centrifuging time in a Hettich Roto Silenta 2 centrifuge was 2 minutes and the speed 3500 rpm. 10 ml of hot wash water was used. The anhydrous betaine crystals were dried in a laboratory oven (Memmert) at 105° C. for 60 minutes. The crystals were then affinated twice with ethanol (AA-grade) for 10-30 minutes and after a similar centrifugation 10 ml of EtOH (AA) was used for washing instead of water. A second drying was performed at 105° C. for 30 minutes.

TABLE 2

Centrifuge yield, crystal purity and run-off purity

| Yield bet/bet | Feed liquid Q | Crystal Q | Aff. 1 yield | Aff. 2 yield | Run off Q |
|---|---|---|---|---|---|
| 59 | 81.9 | 94.8 | 90 | 88 | 71.5 |

Q = purity (betaine w-% of DS) %

The removal of impurities was studied by affination and the results are shown in Table 3a and 3b. The main impurities of the overall impurities were glycerol and amino acids (5.8 w-% of the feed sample, 1.4 w-% of the cake (10 ml wash) and 0.2 w-% of the affinated cake). The amino acids contains also those components which eluates similarly in HPLC analysis. Color removal was 88% after the first wash with water and 94% after affination (calculated by crystal color/mass color).

TABLE 3a

Impurity reductions

| | Glycerol %/DS | reduction % | Impurities %/DS | reduction % |
|---|---|---|---|---|
| Feed sample | 10.1 | | 18.1 | |
| Mass to centrifuge | 9.9 | | 18.0 | |
| Cake (10 ml wash) | 3.1 | 68 | 6.0 | 67 |
| Affinated Cake | 0.5 | 95 | 2.1 | 88 |
| 2 × affinated cake | 0.2 | 98 | 1.0 | 94 |

TABLE 3b

Impurity reductions

| | Color ICUMSA | reduction % | Turbidity ICUMSA | reduction % |
|---|---|---|---|---|
| Feed sample | 10562 | | 1630 | |
| Mass to centrifuge | 23710 | | 3610 | |
| Cake (10 ml wash) | 10875 | 54 | 1702 | 53 |
| Affinated Cake | 2837 | 88 | 1374 | 62 |
| 2 × affinated cake | 1317 | 94 | 1367 | 62 |

This crystalline anhydrous betaine product, for which the betaine content of the 2× affinated cake was 99.0 w-%, did surprisingly not lump even after one month. It was stored at room temperature in a plastic bag.

EXAMPLE 2

Betaine Monohydrate Product from Vinasse

The raw material of these tests was vinasse from Cristal Union (CU) and Tereos (Origny Sainte Benoite plant); separation fractions inclusive glycerol fraction and crystallization run-offs for test No. 2.1 and the run-off from test No. 2.1 for test No. 2.3 and a betaine-glycerol fraction from DK-vinasses SMB-separation for test No. 2.2. Both raw materials were first enriched in SMB combined with SAC-WAC separation. The purity of the feed liquid was about 67 w-% betaine for tests 2.1 and 2.2 and about 54 w-% betaine for test 2.3. The main impurity was glycerol.

TABLE 4

Feed liquid properties, Example 2.1, 2.2 and 2.3

| Test | Color ICUMSA | Turbidity ICUMSA | Betaine (HPLC: Ca++) | Glycerol (HPLC: Na+) |
|---|---|---|---|---|
| 2.1 | 20283 | 932 | 66.9 | 17.9 |
| 2.2 | 33346 | 586 | 67.1 | 13 |
| 2.3 | 84922 | 3771 | 54 | 27.9 |

For test 2.1 the evaporation was carried out in a traditional vacuum crystallizer boiling pan. The temperature during the evaporation was between 94.4° C. and 99.3° C. The pressure in the vacuum pan was in the beginning 489 mbar and was adjusted to 183 mbar in a few hours to maintain the target temperature. Spontaneous seeding started during evaporation at DS 84%. The final dry substance in the evaporation was 88%, after which the mass was dropped to a 100 L traditional cooling crystallizer. A cooling program from 96° C. to 83° C. in 10 hours was started. After 17 hours mixing at about 80° C., the cooling was continued from 80° C. to 42° C. in 10 hours. The first centrifuging tests were carried out at 41° C. Totally 9 kg of mass was moved to a 10 L cooling crystallizer, where the cooling was continued from 41° C. to 31° C. A second centrifuging test was made. The third cooling program was from 35° C. to 25° C. in a 10 L cooling crystallizer.

The masses were centrifuged with a laboratory centrifuge (Hettich Roto Silenta 2) and a pilot centrifuge (Heine centrifuge, max load 25 kg). The wash water amounts were 0, 50 and 100 ml in the laboratory centrifuge and in the pilot centrifuge the washing times were 0 seconds, 2 seconds (300 ml) and 5 seconds (680 ml). The centrifuging time was 2 minutes and speed 3500 rpm for the laboratory centrifuge (d=23 cm) and the time 2 minutes and the speed 2000 rpm for the pilot centrifuge (d=41 cm). Cloth was not used.

The cakes from the pilot centrifuging were dried with a co-current traditional drum dryer. The crystals from the laboratory centrifuge were dried in a laboratory oven in 60° C. for 30 minutes. Drying loss was calculated. Parts of the cakes were not dried in order to test the lumping of a "wet cake". The results of the lumping tests are shown in Example 3.

For test 2.2 the feed liquid was evaporated with a Buchi laboratory rotavapor. The final goal for the dry substance in evaporation was about 89.5%. The mass was put into a 10 L cooling crystallization. A cooling program from 96° C. to 81° C. in 5 hours was started. A new cooling program was started from 81° C. to 31° C. in 5 h. The mass was again let to stabilize over night. In the morning the mass had cooled to 31° C. and a mother liquid sample was centrifuged.

Centrifuging tests were carried out at 31° C. in laboratory. The same laboratory tests were made as for test 2.1.

The cakes were dried in an oven for 30 minutes in 60° C. Drying losses were 0.5% (0 ml wash), 1.2% (50 ml wash) and 1.6% (100 ml wash).

For test 2.3 the feed liquid was evaporated in a Buchi-rotavapor to aim about DS 91.7% mass. Then the mass was moved to a 6-L cooling crystallizer which was pre-heated to 95° C. A cooling program from 95 to 80° C. in 5 hours was started. The mass was mixed overnight at a constant temperature. In the morning a mother liquid sample was taken. Next cooling phase was started from 80° C. to 30° C. in 10 hours. A second mother liquid sample was centrifuged at 55° C. The next morning the third cooling phase was started, from 30° C. to 20° in 4 hours. Centrifuging tests were carried out the next day. The crystals were dried in an oven for 30 minutes in 60° C. The removal of impurities was studied after wash with 0 ml, 50 ml and 100 ml water.

The results for impurity reductions for all tests 2.1 to 2.3 are shown in Tables 5 to 7.

TABLE 5a

Impurity reductions, test 2.1

|  | Glycerol %/DS | reduction % | Impurities %/DS | reduction % | Q HPLC $Ca^{2+}$ |
|---|---|---|---|---|---|
| Laboratory centrifuge, 10 l | | | | | |
| Mass to centrifuge | | | 30.3 | | |
| Cake (0 ml wash) | 2.7 | 85 | 5.7 | 81 | 94.3 |
| Cake (50 ml wash) | 1.3 | 93 | 3.6 | 88 | 96.4 |
| Cake (100 ml wash) | 1.2 | 94 | 2.3 | 92 | 97.7* |
| Pilot centrifuge, 100 l | | | | | |
| Mass to centrifuge | 18.2 | | 30.3 | | |
| Cake (0 s wash) | 3.1 | 83 | 6.4 | 79 | 93.6 |
| Cake (2 s wash) | 1.6 | 91 | 3.7 | 88 | 96.3 |
| Cake (5 s wash) | 1.3 | 93 | 3.1 | 90 | 96.9 |

*HPLC $Na^+$

TABLE 5b

Impurity reductions, test 2.1

|  | Color ICUMSA | reduction % | Turbidity ICUMSA | reduction % |
|---|---|---|---|---|
| Laboratory centrifuge, 10 l | | | | |
| Mass to centrifuge | 51103 | | | |
| Cake (0 ml wash) | 8085 | 84 | 456 | 63 |
| Cake (50 ml wash) | 4410 | 91 | 267 | 79 |
| Cake (100 ml wash) | 3547 | 93 | 269 | 78 |
| Pilot centrifuge, 100 l | | | | |
| Mass to centrifuge | 50772 | | | |
| Cake (0 s wash) | 8604 | 83 | 412 | 67 |
| Cake (2 s wash) | 4442 | 91 | 285 | 77 |
| Cake (5 s wash) | 3876 | 92 | 262 | 79 |

TABLE 6a

Impurity reductions, test 2.2

|  | Glycerol %/DS | reduction % | Impurities %/DS | reduction % | Q HPLC $Ca^{2+}$ |
|---|---|---|---|---|---|
| Mass to centrifuge | 12.9 | | 32.9 | | |
| Cake (0 ml wash) | 3.1 | 76 | 8.5 | 74 | 91.5 |
| Cake (50 ml wash) | 1.2 | 91 | 3.5 | 89 | 96.5 |
| Cake (100 ml wash) | 0.7 | 95 | 1.8 | 94 | 98.2 |

TABLE 6b

Impurity reductions, test 2.2

|  | Color ICUMSA | reduction % | Turbidity ICUMSA | reduction % |
|---|---|---|---|---|
| Mass to centrifuge | 122662 | | | |
| Cake (0 ml wash) | 30184 | 75 | 626 | 60 |
| Cake (50 ml wash) | 11060 | 91 | 275 | 82 |
| Cake (100 ml wash) | 6539 | 94 | 565 | 64 |

TABLE 7a

Impurity reductions, test 2.3

|  | Glycerol %/DS | reduction % | Impurities %/DS | reduction % | Q HPLC $Ca^{2+}$ |
|---|---|---|---|---|---|
| Mass to centrifuge | 27.5 | | 46.0 | | |
| Cake (0 ml wash) | 7.3 | 73 | 11.1 | 76 | 88.9 |
| Cake (50 ml wash) | 2.4 | 91 | 2.9 | 94 | 97.1 |
| Cake (100 ml wash) | 1.3 | 95 | 1.5 | 97 | 98.5 |

TABLE 7b

| | Impurity reductions, test 2.3 | | | |
|---|---|---|---|---|
| | Color ICUMSA | reduction % | Turbidity ICUMSA | reduction % |
| Mass to centrifuge | 89648 | | | |
| Cake (0 ml wash) | 28512 | 68 | 1333 | 70 |
| Cake (50 ml wash) | 10771 | 88 | 818 | 81 |
| Cake (100 ml wash) | 6743 | 92 | 736 | 83 |

The purities of the monohydrate crystalline betaine of tests 2.1, 2.2 and 2.3 were 97.7 w-% for test No. 2.1, 98.2 w-% for test No. 2.2 and 98.5 w-% for test No. 2.3 (HPLC Ca2+)

The analysis results of the feed, the dry cakes after wash as well as the run offs are collected in Table 8a to 8c. The analysis was performed by $Na^+$ and $Ca^{2+}$ HPLC columns. The technical information for the $Na^+$-column (No. 408 078) was 0.6ml/min, +85° C., 0.003M $Na_2(SO)_4$ and for the $Ca^{2+}$-column (No. 1109, Perkin Elmer), 0.8ml/min, +85° C., 0.001M $Ca(NO_3)_2$. It seems from the results that for example the sorbitol peak of the $Ca^{2+}$ column may have been eluted under the betaine peak of the $Na^+$ column. Further the results of the $Ca^{2+}$-column shows a small peak which has not been analyzed and from the betaine-peak a smaller peak was split which may be an amino acid. In the following tables RT stands for components which eluates like amino acids. The abbreviation "sacchar." stands for saccharides and the results comprises both mono- and disaccharides.

TABLE 8a

Analysis results, test No. 2.1

| Sample name | DS(KF) w-% | pH 10% | Colour ICUMSA | Turbidity ICUMSA | Cond. 10% μS/cm | Carbohydrates HPLC, w-%/DS(KF) Na+ | | | | |
|---|---|---|---|---|---|---|---|---|---|---|
| | | | | | | sacchar. mon + di | inositol ino | glycerol gly | betaine Bet | RT |
| Feed | 63.1 | 5.0 | 20283 | 932 | 434 | 1.2 | 0.4 | 17.9 | 70.9 | 5.5 |
| Dry cake 1 (0 s wash) | 88.3 | 5.2 | 8604 | 412 | 133 | 0.0 | 0.1 | 2.9 | 94.0 | 0.5 |
| Run off 1 (0 s wash) | 88.3 | 4.6 | 88630 | 2970 | 973 | 1.1 | 0.8 | 30.0 | 49.3 | 8.1 |
| Mass/centr 2 (2 s wash) | 87.3 | 4.7 | 50772 | 2253 | 618 | 0.6 | 0.5 | 17.9 | 72.1 | 4.6 |
| Dry cake 2 (2 s wash) | 88.7 | 5.4 | 4442 | 285 | 71 | 0.0 | 0.1 | 1.4 | 97.0 | 0.3 |
| Run off 2 (2 s wash) | 85.5 | 4.6 | 81410 | 3536 | 915 | 1.0 | 0.7 | 29.0 | 55.2 | 7.6 |
| Dry cake 3 (5 s wash) | 88.7 | 5.4 | 3876 | 262 | 63 | 0.0 | 0.1 | 1.3 | 98.1 | 0.3 |
| Run off 3 (5 s wash) | 81.4 | 4.6 | 72340 | 2842 | 830 | 0.9 | 0.6 | 25.0 | 58.5 | 6.7 |
| Mass to centrif. 1 (0 ml wash) 10 l | 88.4 | 4.7 | 51103 | 1999 | 612 | 0.6 | 0.5 | 17.5 | 71.3 | 4.9 |
| Dry cake 1 (0 ml wash water) 10 l | 87.6 | 5.2 | 8085 | 456 | 126 | 0.0 | 0.1 | 2.7 | 94.8 | 0.5 |
| Run off 1 (0 ml wash water) 10 l | 88.8 | 4.6 | 95480 | 3374 | 1026 | 1.1 | 0.8 | 33.1 | 48.1 | 8.4 |
| Dry cake 2 (50 ml wash water) 10 l | 87.5 | 5.4 | 4410 | 267 | 73 | 0.0 | 0.0 | 1.4 | 97.1 | 0.2 |
| Run off 2 (50 ml wash water) 10 l | 83.5 | 4.6 | 86918 | 3248 | 945 | 0.8 | 0.8 | 29.7 | 53.1 | 7.6 |
| Dry cake 3 (100 ml wash water) 10 l | 87.1 | 5.5 | 3547 | 269 | 64 | 0.0 | 0.0 | 1.2 | 97.7 | 0.2 |
| Run off 3 (100 ml wash water) 10 l | 78.3 | 4.7 | 73082 | 2578 | 819 | 0.7 | 0.6 | 25.0 | 60.5 | 6.6 |

| Sample name | Carbohydrates HPLC, w-%/DS(KF) Ca2+ | | | | | |
|---|---|---|---|---|---|---|
| | glycerol Gly. | mannitol Man. | sorbitol Sor. | betaine Bet. | gaba+ adenine | other |
| Feed | 17.8 | 2.4 | 3.5 | 66.9 | 0.2 | 1.6 |
| Dry cake 1 (0 s wash) | 3.1 | 0.6 | 0.3 | 93.6 | 0.0 | 0.0 |
| Run off 1 (0 s wash) | 30.1 | 2.1 | 2.2 | 46.0 | 0.2 | 2.2 |
| Mass/centr 2 (2 s wash) | 18.2 | 1.4 | 1.0 | 69.7 | 0.0 | 1.1 |
| Dry cake 2 (2 s wash) | 1.6 | 0.0 | 0.0 | 96.3 | 0.0 | 0.0 |
| Run off 2 (2 s wash) | 29.0 | 2.0 | 1.6 | 51.7 | 0.2 | 2.0 |
| Dry cake 3 (5 s wash) | 1.3 | 0.0 | 0.0 | 96.9 | 0.0 | 0.0 |
| Run off 3 (5 s wash) | 25.3 | 1.8 | 1.9 | 55.5 | 0.0 | 1.7 |
| Mass to centrif. 1 (0 ml wash) 10 l | 18.1 | 1.5 | 1.0 | 69.2 | 0.0 | 0.7 |
| Dry cake 1 (0 ml wash water) 10 l | 2.7 | 0.4 | 0.1 | 94.3 | 0.0 | 0.0 |

TABLE 8a-continued

Analysis results, test No. 2.1

| | | | | | | | |
|---|---|---|---|---|---|---|---|
| Run off 1 (0 ml wash water) 10 l | 33.9 | 2.6 | 2.4 | 44.3 | 0.0 | 1.9 | |
| Dry cake 2 (50 ml wash water) 10 l | 1.3 | 0.3 | 0.1 | 96.4 | 0.0 | 0.0 | |
| Run off 2 (50 ml wash water) 10 l | 30.5 | 2.3 | 2.2 | 49.6 | 0.0 | 1.5 | |
| Dry cake 3 (100 ml wash water) 10 l | 1.1 | 0.3 | 0.1 | 96.0 | 0.0 | 0.0 | |
| Run off 3 (100 ml wash water) 10 l | 25.2 | 1.7 | 1.8 | 57.4 | 0.0 | 1.2 | |

TABLE 8b

Analysis results, test No. 2.2

| | | | | | Cond. | Carbohydrates HPLC, w-%/DS(KF) Na+ | | | | |
|---|---|---|---|---|---|---|---|---|---|---|
| Sample name | DS(KF) w-% | pH 10% | Colour ICUMSA | Turbidity ICUMSA | 10% µS/cm | sacchar. mon + di | inositol ino | glycerol gly | betaine Bet | RT |
| Feed | 51.2 | 6.1 | 33346 | 586 | 979 | 5.2 | 3.0 | 13.0 | 67.3 | 7.2 |
| Dry cake 1 (0 ml wash water) 10 l | 87.3 | 5.2 | 30184 | 626 | 317 | 0.9 | 1.4 | 3.1 | 91.6 | 0.8 |
| Run off 1 (0 ml wash water) 10 l | 88.4 | 4.9 | 228611 | 4274 | 1847 | 5.8 | 5.0 | 24.5 | 42.4 | 9.3 |
| Mass/centr 2 (0 ml wash water) | 87.8 | 5.0 | 122122 | 1958 | 1098 | 3.5 | 3.2 | 13.0 | 68.4 | 5.3 |
| Dry cake 2 (50 ml wash water) 10 l | 86.6 | 5.5 | 11060 | 275 | 130 | 0.4 | 0.7 | 1.2 | 97.4 | 0.1 |
| Run off 2 (50 ml wash water) 10 l | 82.9 | 5.0 | 198672 | 3310 | 1661 | 6.5 | 4.6 | 21.3 | 49.5 | 8.3 |
| Mass/centr 3 (100 ml wash water) 10 l | 88.0 | 4.9 | 125204 | 2025 | 859 | 2.9 | 3.2 | 12.9 | 68.4 | 4.0 |
| Dry cake 3 (100 ml wash water) 10 l | 87.8 | 5.3 | 6539 | 565 | 71 | 0.2 | 0.3 | 0.7 | 97.7 | 0.0 |
| Run off 3 (100 ml wash water) 10 l | 81.0 | 5.0 | 172436 | 2869 | 1459 | 4.9 | 4.0 | 18.2 | 55.4 | 6.7 |

| | Carbohydrates HPLC, w-%/DS(KF) Ca2+ | | | | | | | |
|---|---|---|---|---|---|---|---|---|
| Sample name | Anh. F. | inositol ino | glycerol Gly. | mannitol Man. | sorbitol Sor. | betaine Bet. | gaba+ adenine | other |
| Feed | 2.1 | 4.5 | 14.3 | 0.9 | 0.5 | 67.1 | 0.7 | 1.2 |
| Dry cake 1 (0 ml wash water) 10 l | 0.6 | 1.6 | 3.5 | 0.3 | 0.0 | 91.5 | 0.1 | 0.0 |
| Run off 1 (0 ml wash water) 10 l | 3.7 | 5.0 | 26.9 | 1.8 | 0.7 | 41.9 | 0.8 | 0.8 |
| Mass/centr 2 (0 ml wash water) | 1.9 | 3.1 | 14.1 | 0.8 | 0.4 | 67.6 | 0.4 | 0.4 |
| Dry cake 2 (50 ml wash water) 10 l | 0.3 | 0.8 | 1.3 | 0.2 | 0.0 | 96.5 | 0.0 | 0.0 |
| Run off 2 (50 ml wash water) 10 l | 3.1 | 4.9 | 23.1 | 1.4 | 0.6 | 48.9 | 0.6 | 0.7 |
| Mass/centr 3 (100 ml wash water) 10 l | 2.2 | 3.2 | 14.3 | 1.2 | 0.6 | 69.3 | 0.4 | 0.5 |
| Dry cake 3 (100 ml wash water) 10 l | 0.5 | 0.5 | 0.8 | 0.1 | 0.0 | 98.2 | 0.0 | 0.0 |
| Run off 3 (100 ml wash water) 10 l | 2.9 | 4.4 | 20.0 | 1.2 | 0.5 | 54.9 | 0.6 | 0.6 |

TABLE 8c

Analysis results, test No. 2.3

| | | | | | Cond. | Carbohydrates HPLC, w-%/DS(KF) Na+ | | | | |
|---|---|---|---|---|---|---|---|---|---|---|
| Sample name | DS(KF) w-% | pH 10% | Colour ICUMSA | Turbidity ICUMSA | 10% µS/cm | sacchar. mon + di | inositol ino | glycerol gly | betaine Bet | RT |
| Feed | 70.0 | 4 | 84922 | 3771 | 707 | 0.7 | 0.7 | 27.9 | 55.6 | 7.5 |
| Dry cake 1 (0 ml wash water) 10 l | 86.9 | 4.8 | 28512 | 1333 | 240 | 0.2 | 0.2 | 7.3 | 90.1 | 0.9 |

TABLE 8c-continued

Analysis results, test No. 2.3

| | | | | | | | | | | |
|---|---|---|---|---|---|---|---|---|---|---|
| Run off 1 (0 ml wash water) 10 l | 92.8 | 4.5 | 132300 | 6933 | 950 | 0.8 | 0.9 | 36.5 | 42.2 | 9.2 |
| Mass/centr 2 (50 ml wash water) | 91.3 | 4.5 | 100569 | 5842 | 752 | 0.7 | 0.7 | 28.1 | 56.3 | 7.6 |
| Dry cake 2 (50 ml wash water) 10 l | 86.4 | 5.0 | 10771 | 818 | 100 | 0.0 | 0.1 | 2.4 | 96.7 | 0.6 |
| Run off 2 (50 ml wash water) 10 l | 87.3 | 4.5 | 120479 | 6416 | 849 | 0.8 | 0.9 | 33.5 | 47.4 | 7.8 |
| Dry cake 3 (100 ml wash water) 10 l | 86.7 | 5.1 | 6743 | 736 | 65 | 0.0 | 0.0 | 1.3 | 97.6 | 0.1 |
| Run off 3 (100 ml wash water) 10 l | 84.7 | 4.5 | 118177 | 3168 | 843 | 0.5 | 0.8 | 32.0 | 49.8 | 7.7 |

| | Carbohydrates HPLC, w-%/DS(KF) Ca2+ | | | | | | | |
|---|---|---|---|---|---|---|---|---|
| Sample name | Anh. F. | inositol ino | glycerol Gly. | mannitol Man. | sorbitol Sor. | betaine Bet. | gaba+ adenine | other |
| Feed | 0.6 | 1.0 | 29.7 | 2.2 | 2.2 | 54.0 | 0.2 | 2.2 |
| Dry cake 1 (0 ml wash water) 10 l | 0.0 | 0.1 | 7.9 | 0.6 | 0.5 | 88.9 | 0.0 | 0.0 |
| Run off 1 (0 ml wash water) 10 l | 0.6 | 0.9 | 38.8 | 2.3 | 2.1 | 40.3 | 0.3 | 2.3 |
| Mass/centr 2 (50 ml wash water) | 0.5 | 0.7 | 29.8 | 1.9 | 1.7 | 54.8 | 0.0 | 1.8 |
| Dry cake 2 (50 ml wash water) 10 l | 0.0 | 0.0 | 2.6 | 0.2 | 0.1 | 97.1 | 0.0 | 0.0 |
| Run off 2 (50 ml wash water) 10 l | 0.6 | 1.0 | 35.9 | 2.2 | 1.5 | 45.7 | 0.2 | 2.1 |
| Dry cake 3 (100 ml wash water) 10 l | 0.0 | 0.0 | 1.2 | 0.0 | 0.0 | 98.5 | 0.0 | 0.0 |
| Run off 3 (100 ml wash water) 10 l | 0.4 | 0.8 | 34.1 | 2.1 | 1.8 | 48.1 | 0.3 | 2.1 |

EXAMPLE 3

Lumping Tests

The crystalline monohydrate betaine of Example 2 (Tests No. 2.1 and 2.2) were monitored for four to eight weeks to see if the products get stiffened, hard or lumpy over time.

The products where kept in plastic bags (15×10×1.5 cm), in glass jars and in closed plastic buckets. Some of the products where kept under a weight (1 kg per 150 cm²) for the time indicated in Table 9a to 9c. The amount of wash, how the crystals where dried, the purity (by HPLC Na$^{30}$) and color of each product as well as the amount of water and the lumpiness after four to eight weeks for each test are shown in Table 8.

As can be seen from the results the purity, i.e. the amount of betaine was between 91.6 and 98.1 for the different tests. None of the solid betaine products formed hard lumps independently of whether they were stored in plastic bags, glass jars or plastic buckets. As can be seen for example for tests A1 to F1, not even storage under pressure of a weight led to the formation of hard lumps.

Soft lumps as defined in the table are lumps which can be broken by firmly touching the lumps.

TABLE 9a

Yield crystallization 2.1, 100 l cooling crystallization (41° C. centrifugation)

| | | | | | | | | Storage period 8 weeks | | |
|---|---|---|---|---|---|---|---|---|---|---|
| Purity HPLC Ca$^{2+}$ | Purity, color Na$^+$, Icumsa | test | | storage | wash/s | drying | weight/g | Use of weight | Lumpiness |
| 93.6 | 94.0 | 8600 | 1A | 1. cake | bag | 0 | oven dried | 230 | 3.0 weeks | Totally separate |
| | | | 1B | 1. cake | bag | 0 | no drying | 230 | 3.0 weeks | Totally separate |
| 96.3 | 97.0 | 4400 | 1C | 2. cake | bag | 2 s | drum dried | 230 | 3.0 weeks | Totally separate |
| | | | 1D | 2. cake | bag | 2 s | no drying | 230 | 3.0 weeks | Totally separate |
| 96.9 | 98.1 | 3800 | 1E | 3. cake | bag | 5 s | no drying | 230 | 3.0 weeks | Totally separate |
| | | | 1F | 3. cake | bag | 5 s | drum dried | 230 | 3.0 weeks | Totally separate |
| 94.0 | 94.0 | 8600 | 2A | 1. cake | jar | 0 | oven dried | 50 | closed | Totally separate |
| | | | 2B | 1. cake | jar | 0 | no drying | 50 | closed | Totally separate |
| 97.0 | 97.0 | 4400 | 2C | 2. cake | jar | 2 s | drum dried | 50 | closed | Totally separate |
| | | | 2D | 2. cake | jar | 2 s | no drying | 50 | closed | Sticky, soft lumps |
| 98.1 | 98.1 | 3800 | 2E | 3. cake | jar | 5 s | no drying | 50 | closed | Sticky, soft lumps |
| | | | 2F | 3. cake | jar | 5 s | drum dried | 50 | closed | Totally separate |
| 94.0 | 94.0 | 8600 | 3A | 1. cake | bag | 0 | oven dried | 230 | no | Totally separate |
| | | | 3B | 1. cake | bag | 0 | no drying | 230 | no | Totally separate |
| 97.0 | 97.0 | 4400 | 3C | 2. cake | bag | 2 s | drum dried | 230 | no | Totally separate |
| | | | 3D | 2. cake | bag | 2 s | no drying | 230 | no | Totally separate |

TABLE 9a-continued

Yield crystallization 2.1, 100 l cooling crystallization (41° C. centrifugation)

| Purity HPLC $Ca^{2+}$ | Purity, color $Na^+$, Icumsa | test | storage | wash/s | drying | weight/g | Storage period 8 weeks Use of weight | Lumpiness |
|---|---|---|---|---|---|---|---|---|
| 98.1 | 98.1 3800 | 3E 3. cake | bag | 5 s | no drying | 230 | no | Totally separate |
|  | 3F | 3. cake | bag | 5 s | drum dried | 230 | no | Totally separate |
|  |  |  | bucket | 2 s | drum dried | 16 kg | closed | Totally separate |
|  |  |  | bucket | 2 s | no drying | 2 kg | closed | Sticky, soft lumps |
|  |  |  | bucket | 5 s | drum dried | 3 kg | closed | soft lumps |
|  |  |  | bucket | 5 s | no drying | 1 kg | closed | Sticky, soft lumps |
|  |  |  | bucket | middle fraction 2/5 s | drum dried | 1.4 kg | closed | Totally separate |
|  |  | centrifugation | bucket | 2 s | drum dried | 6.3 kg | closed | Totally separate |

TABLE 9b

Yield crystallization 2.1, 10 l cooling crystallization, (30° C. centrifugation)

| Purity HPLC $Ca^{2+}$ | Purity $Na^+$, color | test | storage | wash/ml | drying | weight, g | Storage period 8 weeks Use of weight | Lumpiness |
|---|---|---|---|---|---|---|---|---|
| 94.3 | 94.8 8100 | A1 1. cake | Bag | 0 | oven dried | 230 | 8.1 weeks | Totally separate |
|  | B1 | 1. cake | Bag | 0 | no drying | 230 | 8.1 weeks | Totally separate |
| 96.4 | 97.1 4400 | C1 2. cake | bag | 50 ml | oven dried | 230 | 8.1 weeks | Totally separate |
|  | D1 | 2. cake | bag | 50 ml | no drying | 230 | 8.1 weeks | Totally separate |
| — | 97.7 3500 | E1 3. cake | bag | 100 ml | oven dried | 230 | 8.1 weeks | Totally separate |
|  | F1 | 3. cake | bag | 100 ml | no drying | 230 | 8.1 weeks | Sticky, soft lumps |
| 94.8 | 94.8 8100 | A2 1. cake | jar | 0 | oven dried | 50 | closed | Totally separate |
|  | B2 | 1. cake | jar | 0 | no drying | 50 | closed | Totally separate |
| 97.1 | 97.1 4400 | C2 2. cake | jar | 50 ml | oven dried | 50 | closed | Totally separate |
|  | D2 | 2. cake | jar | 50 ml | no drying | 50 | closed | Sticky, soft lumps |
| 97.7 | 97.7 3500 | E2 3. cake | jar | 100 ml | oven dried | 50 | closed | Totally separate |
|  | F2 | 3. cake | jar | 100 ml | no drying | 50 | closed | Sticky, soft lumps |
|  | F3 | 3. cake | bag | 100 ml | no drying | 20 | no | Totally separate |
|  |  | 2. cake | closed bucket | 50 ml | no drying | 0.2 kg | closed | Sticky, soft lumps |
|  |  | 3. cake dried | closed bucket | 100 ml | oven dried | 0.01 kg | closed | Totally separate |

TABLE 9c

Yield crystallization 2.2, 10 l cooling crystallization, (31° C. centrifugation)

| Purity HPLC $Ca^{2+}$ | Purity $Na^+$, color | test | storage | wash/ml | drying | weight/g | Storage period 4 weeks Use of weight | Lumpiness |
|---|---|---|---|---|---|---|---|---|
| 91.5 | 91.6 30200 | 1. cake, dried | bucket | 0 | oven dried | 500 g | closed | Totally separate |
| 96.5 | 97.4 11000 | 2 + 4. cake, dried | bucket | 50 ml | oven dried | 1 kg | closed | Totally separate |
| 98.2 | 97.7 7300 | 3. cake dried | bucket | 100 ml | oven dried | 200 g | closed | Totally separate |

EXAMPLE 4

Melting Efficiency

In this test, the melting efficiency of different combinations of ice-melting agents and different mixture ratios were compared to each other in relation to time. In this test the penetration efficiency into ice in relation to time was measured in millimeters (mm) by adding liquid and solids onto the surface. The dept of the hole was measured at 10, 30 and 60 minutes after the addition of the liquid solution or solid compound. The test temperatures were −2° C. and −6° C. respectively during the tests. The results are shown in Table 10 and Table 11.

TABLE 10

The melting efficiency (mm) of different liquid and solid ice-melting agents at −2° C.

|  | 10 minutes | 30 minutes | 60 minutes |
|---|---|---|---|
| Liquids |  |  |  |
| Betaine (50 w-%) | 2.1 | 3.6 | 4.8 |
| KAc (50 w-%) | 3.9 | 7.6 | 10.2 |
| Solids |  |  |  |
| Betaine | 3.1 | 5.3 | 7.2 |
| Urea | 2.4 | 5.8 | 8.9 |

TABLE 11

The melting efficiency (mm) of different liquid and
solid ice-melting agents at −6° C.

|  | 10 minutes | 30 minutes | 60 minutes |
|---|---|---|---|
| Liquids |  |  |  |
| Betaine (50 w-%) | 1.6 | 2.4 | 2.9 |
| KAc (50 w-%) | 3.6 | 6.1 | 6.7 |
| Solids |  |  |  |
| Betaine | 2.6 | 4.3 | 5.5 |
| Urea | 2.3 | 5.7 | 7.9 |

EXAMPLE 5

Granulation of Betaine

A 60% betaine solution was atomized in a fluid bed (AGT 150) and the growth of particles was monitored. The inlet temperature was 120° C., the bed temperature was 75° C. and the moisture content 5%. The grain size was controlled by adding seeds continuously during the granulation process. The input of seeds was more than 50% of total betaine.

The grain size distribution is shown in Table 12.

TABLE 12

Grain size distribution

| Grain size, μm | | Test No. | | | | |
|---|---|---|---|---|---|---|
|  |  | 5.0 Start filling % | 5.1 % | 5.2 % | 5.3 % | 5.4 % | 5.5 Rest layer % |
|  | >3150 | 0.00 | 0.00 | 0.00 | 0.00 | 0.00 | 0.00 |
| 2500 | 3150 | 0.00 | 0.00 | 0.00 | 0.00 | 0.00 | 0.00 |
| 2000 | 2500 | 0.00 | 0.00 | 0.00 | 0.00 | 0.00 | 1.60 |
| 1600 | 2000 | 0.00 | 0.00 | 0.00 | 0.00 | 1.01 | 0.90 |
| 1250 | 1600 | 0.00 | 0.00 | 0.00 | 0.00 | 3.90 | 4.01 |
| 1000 | 1250 | 0.00 | 1.00 | 3.20 | 10.81 | 38.93 | 12.42 |
| 800 | 1000 | 0.20 | 6.79 | 20.02 | 28.73 | 28.60 | 17.03 |
| 630 | 800 | 1.20 | 49.05 | 43.84 | 32.13 | 15.81 | 16.33 |
| 500 | 630 | 17.32 | 31.07 | 23.32 | 20.32 | 8.22 | 7.92 |
| 400 | 500 | 17.92 | 7.59 | 6.71 | 5.61 | 2.31 | 3.41 |
| 315 | 400 | 12.31 | 2.60 | 2.30 | 1.90 | 0.90 | 12.83 |
| 250 | 315 | 12.91 | 0.50 | 0.20 | 0.20 | 0.13 | 12.53 |
| 200 | 250 | 21.82 | 0.30 | 0.20 | 0.10 | 0.05 | 7.41 |
| 160 | 200 | 6.71 | 0.30 | 0.10 | 0.10 | 0.07 | 2.51 |
| 100 | 160 | 6.61 | 0.30 | 0.10 | 0.10 | 0.05 | 1.00 |
| 63 | 100 | 3.00 | 0.20 | 0.00 | 0.00 | 0.01 | 0.10 |
| 0 | 63 | 0.00 | 0.30 | 0.00 | 0.00 | 0.00 | 0.00 |
| Mean grain size, μm |  | 339.00 | 640.94 | 696.52 | 752.90 | 936.90 | 678.63 |
| Density, g/l |  | 530.00 | 530.00 | 525.00 | 510.00 | 515.00 | 570.00 |
| Moisture % |  | 2.42 | 3.82 | 5.32 | 5.11 | 6.42 | 4.37 |

EXAMPLE 6

Spreading Test

The monohydrate crystalline betaine was prepared from the runoff of molasses from the Finnfeeds Finland production facility in Naantali, Finland.

For test 6.1 the feed liquid was evaporated in a traditional vacuum boiling pan until crystals formed. Then the mass was moved to a 400 l cooling crystallizer which was pre-heated to 98° C. A cooling program from 98 to 84° C. in 15 hours was started. The next cooling phase was started from 84° C. to 40° C. in 10 hours. Centrifuging tests were carried out the next day in a pilot centrifuge (Heine centrifuge, max load 25 kg). The centrifuging mass in the centrifuge was 10680 g and the cake was 5100 g. The washing time was 2 seconds, the centrifuging time 5 minutes and speed 2000 rpm (d=41 cm). The crystals were dried in a traditional co-current drum drier, the temperature of the drying air was 50 to 55° C. 188 kg of solid betaine was packed in a flexible bulk container. The mean particle size of the drum dried product was 660 pm (coefficient of variation 21%).

For test 6.2 the feed liquid was evaporated in a traditional vacuum boiling pan until crystals formed. Then the mass was moved to a 100 l and 10 l cooling crystallizer which was pre-heated to 98° C. A cooling program from 92.5 to 85° C. in 20 hours was started. The next cooling phase was started from 85° C. to 40° C. in 10 hours. A third cooling program was started from 40 to 30° C. in 5 hours. Centrifuging tests were carried out in a pilot centrifuge (Heine centrifuge, max load 25 kg). The centrifuging mass in the centrifuge was 11080 g and the cake was 5570 g for the 100 l cooling crystallizer. The washing time was 2 seconds, the centrifuging time 5 minutes and speed 2000 rpm (d=41 cm). The crystals were dried in an oven. The mean particle size of the drum dried product was 705 μm (coefficient of variation 16%).

For test 6.3 the feed liquid was evaporated in a traditional vacuum boiling pan until crystals formed. Then the mass was moved to a 400 l cooling crystallizer which was pre-heated to 98° C. A cooling program from 96.5 to 83° C. in 10 hours was started. The next cooling phase was started from 83° C. to 35° C. in 15 hours. Centrifuging tests were carried out in a pilot centrifuge (Heine centrifuge, max load 25 kg). The centrifuging mass in the centrifuge was 12720 g and the cake was 4990 g for the 100 l cooling crystallizer. The washing time was 4 seconds, the centrifuging time 5 minutes and speed 2000 rpm (d=41 cm). The crystals were dried in a traditional co-current drum drier, the temperature of the drying air was in 30 to 40° C. The dried betaine was screened through a 1.5 mm sieve and 60.3 kg of solid betaine was received. The mean particle size of the drum dried and screened product was 622 μm (coefficient of variation 17%).

The analysis results of the feed, the dry cakes after wash as well as the run offs are collected in Table 13a to 13c. The analysis was performed by a Ca$^{2+}$ HPLC column.

TABLE 13a

Analysis results, test No. 6.1

| Sample name | DS(KF) w-% | pH 10% | Colour ICUMSA | Turbidity ICUMSA | Cond. 10% µS/cm | Carbohydrates HPLC, w-%/DS(KF) Ca$^{2+}$ ||||
|---|---|---|---|---|---|---|---|---|---|---|
| | | | | | | sacchar. mon + di | 7 min Rt* | Glucose Glu | Anh. F. | Ino |
| Feed | 58.4 | 8.9 | 86068 | 2504 | 3051 | 2.2 | 1.4 | 0.0 | 3.1 | 4.3 |
| Seeding | 83.6 | 8.6 | 85745 | 6706 | 3053 | 2.2 | 0.8 | 0.7 | 0.1 | 4.2 |
| Mass to centrif. | 86.2 | 8.7 | 89982 | 3781 | 3054 | | | | | |
| Dry cake (2 s drying) | 90.5 | 8.1 | 8794 | 1733 | 391 | 0.2 | 0.1 | 0.0 | 0.3 | 0.9 |
| Run off (2 s) | 82.2 | 8.8 | 166078 | 4337 | 5200 | 4.1 | 1.4 | 1.4 | 5.8 | 7.6 |

| Sample name | Carbohydrates HPLC, w-%/DS(KF) Ca$^{2+}$ ||||||||| |
|---|---|---|---|---|---|---|---|---|---|
| | Erytritol Eryt. | glycerol Gly. | mannitol Man. | sorbitol Sor. | Adenosine Adeno | betaine Bet. | Proline Prol | Gaba | other |
| Feed | 0.1 | 3.7 | 2.6 | 0.4 | 0.3 | 72.2 | 1.0 | 0.7 | 0.2 |
| Seeding | 0.1 | 3.6 | 2.6 | 0.4 | 0.3 | 71.6 | 1.0 | 0.8 | 0.1 |
| Mass to centrif. | | | | | | | | | |
| Dry cake (2 s drying) | 0.0 | 0.3 | 0.4 | 0.4 | 0.0 | 94.8 | 0.1 | 0.0 | 0.0 |
| Run off (2 s) | 0.3 | 7.0 | 4.9 | 0.7 | 0.7 | 48.2 | 1.7 | 1.5 | 0.2 |

Rt = retention time

TABLE 13b

Analysis results, test No. 6.2

| Sample name | DS(KF) w-% | pH 10% | Colour ICUMSA | Turbidity ICUMSA | Cond. 10% µS/cm | Carbohydrates HPLC, w-%/DS(KF) Ca$^{2+}$ ||||
|---|---|---|---|---|---|---|---|---|---|---|
| | | | | | | sacchar. mon + di | 7 min Rt* | Glucose Glu | Anh. F. | Ino |
| Seeding | 83.4 | 8.9 | 83842 | 7005 | 2977 | 2.1 | 0.6 | 0.6 | 3.1 | 4.3 |
| Mass to centrif. | 85.8 | 8.8 | 88207 | 3176 | 3029 | | | | | |
| Dry cake (2 s drying) | 86.5 | 8.0 | 8672 | 1778 | 373 | 0.2 | 0.1 | 0.0 | 1.9 | 1.9 |
| Run off (2 s) | 75.9 | 8.8 | 167784 | 7075 | 5390 | 4.1 | 1.1 | 1.1 | 5.7 | 6.9 |
| 10 l/Dry cake (2 s drying) | 86.6 | 8.1 | 10230 | 1699 | 458 | 0.2 | 0.1 | 0.0 | 0.1 | 1.2 |

| Sample name | Carbohydrates HPLC, w-%/DS(KF) Ca$^{2+}$ ||||||||| |
|---|---|---|---|---|---|---|---|---|---|
| | Erytritol Eryt. | glycerol Gly. | mannitol Man. | sorbitol Sor. | Adenosine Adeno | betaine Bet. | Proline Prol | Gaba | other |
| Seeding | 0.2 | 3.9 | 2.9 | 0.4 | 0.3 | 71.8 | 1.0 | 0.9 | 0.2 |
| Mass to centrif. | | | | | | | | | |
| Dry cake (2 s drying) | 0.0 | 0.4 | 0.4 | 0.0 | 0.0 | 96.6 | 0.0 | 0.0 | 0.0 |
| Run off (2 s) | 0.3 | 7.0 | 5.0 | 0.7 | 0.7 | 46.8 | 1.9 | 1.2 | 0.9 |
| 10 l/Dry cake (2 s drying) | 0.0 | 0.2 | 0.3 | 0.0 | 0.0 | 96.8 | 0.0 | 0.0 | 0.0 |

TABLE 13c

Analysis results, test No. 6.3

| Sample name | DS(KF) w-% | pH 10% | Colour ICUMSA | Turbidity ICUMSA | Cond. 10% μS/cm | Carbohydrates HPLC, w-%/DS(KF) Ca²⁺ | | | | |
|---|---|---|---|---|---|---|---|---|---|---|
| | | | | | | sacchar. mon + di | 7 min Rt* | Glucose Glu | Anh. F. | Ino |
| Seeding | 84.2 | 8.8 | 82247 | 8946 | 2983 | 2.1 | 0.6 | 0.6 | 2.9 | 4.1 |
| Mass to centrif. | 85.2 | 8.7 | 92894 | 3377 | 3061 | | | | | |
| Dry cake (2 s drying) | 88.5 | 7.8 | 3440 | 941 | 160 | 0.0 | 0.0 | 0.0 | 0.0 | 0.1 |
| Run off (2 s) | 75.9 | 8.7 | 150352 | 4519 | 4840 | 3.5 | 1.0 | 1.0 | 4.9 | 7.0 |
| Drum dried crystal (2 × 2 s) | 86.8 | 7.4 | 3392 | 908 | 150 | 0.0 | 0.0 | 0.0 | 0.0 | 0.1 |

| Sample name | Carbohydrates HPLC, w-%/DS(KF) Ca²⁺ | | | | | | | | |
|---|---|---|---|---|---|---|---|---|---|
| | Erytritol Eryt. | glycerol Gly. | mannitol Man. | sorbitol Sor. | Adenosine Adeno | betaine Bet. | Proline Prol | Gaba | other |
| Seeding Mass to centrif. | 0.2 | 3.5 | 2.6 | 0.2 | 0.3 | 71.3 | 1.0 | 0.6 | 0.1 |
| Dry cake (2 s drying) | 0.0 | 0.0 | 0.1 | 0.0 | 0.0 | 99.0 | 0.0 | 0.0 | 0.0 |
| Run off (2 s) | 0.3 | 6.0 | 4.4 | 0.6 | 0.6 | 53.4 | 1.5 | 1.1 | 0.1 |
| Drum dried crystal (2 × 2 s) | 0.0 | 0.0 | 0.1 | 0.0 | 0.0 | 99.4 | 0.0 | 0.0 | 0.0 |

The solid betaine of tests 6.1 and 6.2 were transported in two flexible intermediate bulk containers (750 kg and 250 kg). The flexible sacks were raised above the car with the spreading equipment and broken on a fixed thorn. This solid betaine only had soft lumps and could easily be moved to the spreading equipment and be spread out in normal humid conditions without lumping in the equipment.

The solid betaine was spread out as such and together with a 50 w-% solution of an aqueous liquid betaine solution (300/700 proportion of liquid/solid). It was cloudy during the spreading test and the temperature in the air was −3° C. and the surface temperature was 0.5° C.

The solid monohydrate betaine was spread out as such and together with an aqueous betaine (50 w-%) liquid solution. Together with the solution the dust effect was smaller and a further advantage compared to only using a betaine solution is the higher concentration of betaine which can be spread out to improve the melting capacity without affecting the amount of liquid needed. The spreading was made at a distance of 3 km and approximately 35 g/m². The spreading width was measured to be 4.6 m, 5.5 m and approximately 7 m.

Brushing of the treated area was performed after about one hour. Tire marks had softened from the surface and here and there the asphalt was plain. The brushing result was fairly good.

The present invention has been described herein with reference to specific embodiments. It is however clear to those skilled in the art that the process(es) may be varied within the bounds of the claims.

The invention claimed is:

1. A method for de-icing a surface having ice thereon, method comprising applying to said surface a sufficient amount of a solid betaine product that comprises betaine and at least one non-betaine compound affecting water or moisture movement in said solid betaine product.

2. The method according to claim 1 wherein said solid betaine product comprises anhydrous or monohydrate crystalline betaine or a combination thereof.

3. The method according to claim 1 wherein said solid betaine product is prepared from a feed liquid comprising said at least one non-betaine compound.

4. The method according to claim 1 wherein said solid betaine product is coated prior to use.

5. The method according to claim 1 wherein the mean particle size of said solid betaine product is 0.5 to 4 mm.

6. The method according to claim 1 wherein said solid betaine can be stored and applied under humid conditions.

7. The method according to claim 1 wherein said solid betaine product comprises 90 to 99.5 w-% of betaine by dry substance.

8. The method according to claim 7 wherein said solid betaine product comprises 0.1 to 7 w-% of at least one of said non-betaine compounds affecting water or moisture movement in said solid betaine product.

9. The method according to claim 1 wherein said solid betaine product is used in combination with an aqueous de-icing solution.

10. The method according to claim 9 wherein said aqueous de-icing solution comprises 35 to 65 w-% of water.

11. The method according to claim 10 wherein said aqueous de-icing solution comprises betaine.

12. The method according to claim 11 wherein said aqueous de-icing solution comprises 45 to 55 w-% of betaine.

13. The method according to claim 9 wherein said solid betaine product is applied at the same time as said solution.

14. The method according claim 9 wherein said solid betaine product is applied before said solution.

15. The method according to claim 9 wherein said solution is applied before said solid betaine product.

16. The method according to claim 1 wherein said solid betaine product is used in combination with another ice-melting agent selected from the group consisting of acetates, formates, urea, propanediol and mixtures thereof.

17. The method according to claim 16 wherein said another ice-melting product is used in solid form or in the form of a solution.

18. The method of claim 1, wherein said solid betaine product is a non- or soft-lumping product.

19. The method of claim 1, wherein said solid betaine product is in the form of crystals or particulates.

20. The method of claim 5, wherein the mean particle size of said solid betaine product is 0.8 to 2.5 mm.

21. The method of claim 5, wherein the mean particle size of said solid betaine product is 1 to 1.5 mm.

22. The method of claim 8, wherein said solid betaine product comprises 0.1 to 5 w-% of said at least one non-betaine compound.

23. The method of claim 8, wherein said solid betaine product comprises 0.1 to 2 w-% of said at least one non-betaine compound.

24. The method of claim 8, wherein said solid betaine product comprises 0.1 to 1 w-% of said at least one non-betaine compound.

25. The method of claim 10, wherein said aqueous de-icing solution comprises 45 to 65 w-% of water.

26. The method of claim 12, wherein said aqueous de-icing solution comprises about 50 w-% of betaine.

27. The method of claim 16, wherein said another ice-melting product is administered before, after, or at the same time as said solid betaine product.

28. A process for the manufacture of a solid betaine product that comprises betaine and at least one non-betaine compound affecting water or moisture movement in said solid betaine product, the method comprising:
   a. preparing a suspension comprising betaine crystals and said at least one non-betaine compound from a feed liquid comprising same, and
   b. separating said betaine crystals and said at least one non-betaine compound from said feed liquid and washing said betaine crystals and said at least one non-betaine compound under wash conditions that provide 0.5 to 10 w-% of said at least one non-betaine compound in said solid betaine product.

29. The process according to claim 28 wherein said solid betaine product comprises 0.1 to 7 w-% of said at least one non-betaine compound affecting water or moisture movement in said solid betaine product.

30. The process according to claim 28 wherein said solid betaine product comprises anhydrous or monohydrate crystalline betaine or a mixture thereof.

31. The process according to claim 28 wherein said at least one non-betaine compound is naturally found in said feed liquid.

32. The process according to claim 28 further comprising the step of granulating the solid betaine product.

33. The process according to claim 28 further comprising the step of coating said solid betaine product.

34. The process according to claim 33 wherein said solid betaine product is coated with a polymer.

35. The process according to claim 34 wherein said polymer is polyvinyl alcohol (PVA), carboxymethyl cellulose (CMC) or other water-soluble polymers.

36. The process according to claim 28 wherein the mean particle size of said solid betaine product is 0.5 to 4 mm.

37. The process according to claim 29 wherein said solid betaine product comprises 0.1 to 5 w-% of said at least one non-betaine compound affecting water or moisture movement in said solid betaine product.

38. The process according to claim 29 wherein said solid betaine product comprises 0.1 to 2 w-% of said at least one non-betaine compound affecting water or moisture movement in said solid betaine product.

39. The process according to claim 29 wherein said solid betaine product comprises 0.1 to 1 w-% of said at least one non-betaine compound affecting water or moisture movement in said solid betaine product.

40. The process according to claim 28 wherein said solid betaine product is non- or soft-lumping.

41. The process according to claim 28 wherein said feed liquid is molasses or vinasse.

* * * * *